(12) United States Patent
Kim et al.

(10) Patent No.: US 12,296,075 B2
(45) Date of Patent: May 13, 2025

(54) FLUID PROCESSING MODULE AND STORAGE DEVICE COMPRISING FLUID PROCESSING MODULE

(71) Applicant: SEOUL VIOSYS CO., LTD., Gyeonggi-do (KR)

(72) Inventors: Ji Won Kim, Gyeonggi-do (KR); Jae Hak Jeong, Gyeonggi-do (KR); Sang Cheol Shin, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 739 days.

(21) Appl. No.: 17/334,277

(22) Filed: May 28, 2021

(65) Prior Publication Data

US 2021/0283297 A1    Sep. 16, 2021

Related U.S. Application Data

(63) Continuation of application No. PCT/KR2019/016752, filed on Nov. 29, 2019.

(30) Foreign Application Priority Data

Nov. 30, 2018    (KR) .................... 10-2018-0152797

(51) Int. Cl.
*A61L 9/20*    (2006.01)
*F25D 17/04*    (2006.01)

(52) U.S. Cl.
CPC .............. *A61L 9/205* (2013.01); *F25D 17/04* (2013.01); *A61L 2209/12* (2013.01); *A61L 2209/14* (2013.01)

(58) Field of Classification Search
CPC .. A61L 9/205; A61L 2009/12; A61L 2009/14; A61L 2009/134; A61L 2009/11;
(Continued)

(56) References Cited

U.S. PATENT DOCUMENTS 4,102,654 A * 7/1978 Pellin ..................... H01T 23/00
                                                            422/24
5,078,971 A * 1/1992 Matuda .................. B01D 53/38
                                                            422/306
(Continued)

FOREIGN PATENT DOCUMENTS

JP    2003180805 A    7/2003
JP    2003310724       11/2003
(Continued)

OTHER PUBLICATIONS

Machine Translation of JP 2003/180805 A, cited in IDS filed Jun. 6, 2023 (Year: 2003).*

(Continued)

*Primary Examiner* — Jennifer Wecker
*Assistant Examiner* — Brady C Pilsbury
(74) *Attorney, Agent, or Firm* — Perkins Coie LLP

(57) ABSTRACT

A fluid processing module includes a main body having a flow channel extending in a first direction therein and allowing a fluid to flow therein, an absorption filter disposed perpendicular to the first direction inside the main body, a photocatalyst filter disposed parallel to the first direction inside the main body, and a light source unit disposed inside the main body and emitting light towards the photocatalyst filter. The fluid flows at a first flow rate in the region of the flow channel having a first cross-sectional area. The fluid flows at a second flow rate in the region of the flow channel having a second cross-sectional area. The photocatalyst filter has effective deodorizing efficiency when the fluid flows at the second flow rate.

18 Claims, 11 Drawing Sheets

(58) Field of Classification Search
CPC ... A61L 2009/22; F25D 17/04; F25D 17/042; F25D 2317/0415; F25D 2317/0417
See application file for complete search history.

(56) References Cited

U.S. PATENT DOCUMENTS

| | | | | |
|---|---|---|---|---|
| 5,933,702 | A * | 8/1999 | Goswami | F24F 3/12 422/186.3 |
| 7,674,436 | B1 * | 3/2010 | Feldman | A61L 9/205 55/482 |
| 9,675,726 | B2 * | 6/2017 | Lunman | A61L 9/20 |
| 10,279,068 | B2 * | 5/2019 | Eide | B01D 53/30 |
| 2008/0286163 | A1 * | 11/2008 | Garfield | A61L 9/205 427/532 |

FOREIGN PATENT DOCUMENTS

| | | |
|---|---|---|
| JP | 2013180178 | 9/2013 |
| KR | 100826320 | 5/2008 |
| KR | 101212713 | 12/2012 |
| KR | 101434562 | 8/2014 |
| WO | 2018208098 A1 | 11/2018 |

OTHER PUBLICATIONS

Ueyama A., "Basic Course of Thermo-Fluid Analysis 06: Chapter 3 Basics of Flow—3.2.1 Compressible/incompressible fluids", Hexagon (Year: 2019).*
Webpage titled "Venturi" published by Lenntech (Year: 2023).*
Updated Machine Translation of JP 2003/180805 A, Sakurada (Year: 2003).*
International Search Report for International Application PCT/KR2019/016752, mailed Mar. 17, 2020.
Office Action from corresponding Chinese Patent Application No. 201980043759.9, dated Sep. 14, 2022 (8 pages).
English Translation of Office Action from corresponding Chinese Patent Application No. 201980043759.9, dated Mar. 26, 2023 (7 pages).

* cited by examiner

FLUID PROCESSING MODULE AND STORAGE DEVICE COMPRISING FLUID PROCESSING MODULE

CROSS-REFERENCE OF RELATED APPLICATIONS AND PRIORITY

The Present Application is a continuation of International Application No. PCT/KR2019/016752 filed Nov. 29, 2019 which claims priority to Korean Patent Application No. 10-2018-0152797 filed Nov. 30, 2018, the disclosure of which are incorporated by reference herein in their entirety.

TECHNICAL FIELD

Embodiments of the present disclosure relate to a fluid processing module and a storage device including the same.

BACKGROUND

In recent years, as air pollutants including fine dusts increase, interest and demands in air purification are increasing. Air purifiers for purification of indoor air have been getting primary attention. However, there is also a need for deodorization and sterilization of air inside closed storage devices, such as refrigerators, closets, and the like. In particular, air circulation is limited or restricted in such a closed storage device, and pollutants entering the storage device may not be treated and remain in an untreated state. Air inside the storage device contaminated by such pollutants can provide an adverse effect on all indoor air.

There are several considerations to be taken in purifying air inside the closed storage device. First, since an interior space of the storage device has a restricted size, a fluid processing module for air purification having a compact structure is desirable. However, when the fluid processing module is made compact, fluid processing efficiency and a fluid processing amount per hour can be reduced.

Therefore, there is a need for a fluid processing module having a compact structure while improving fluid processing efficiency.

SUMMARY

Embodiments of the present disclosure provide a fluid processing module that secures high efficiency in operation without power consumption by preventing loss in flow speed upon fluid processing, such as deodorization, sterilization, and the like, and a storage device including the fluid processing module.

Embodiments of the present disclosure provide a fluid processing module having a compact structure to provide high space utilization.

In accordance with one aspect of the present disclosure, a fluid processing module includes a main body having a flow channel extending in a first direction therein and allowing a fluid to flow therein, an absorption filter disposed perpendicular to the first direction inside the main body; a photocatalyst filter disposed parallel to the first direction inside the main body, and a light source unit disposed inside the main body and emitting light towards the photocatalyst filter. The flow channel has a first cross-sectional area in a region where the absorption filter is disposed and a second cross-sectional area in a region where the photocatalyst filter is disposed. The fluid flows at a first flow speed in the region of the flow channel having the first cross-sectional area and at a second flow speed in the region of the flow channel having the second cross-sectional area. When the fluid flows at the second flow speed in the region of the flow channel where the photocatalyst filter is disposed, the photocatalyst filter has effective deodorization efficiency. The effective deodorization efficiency may indicate a predetermined level of deodorization efficiency exhibited by the photocatalyst filter.

In at least one variant, the main body further includes a guide portion defining the flow channel.

In another variant, the flow channel has a smaller cross-sectional area in a region where the guide portion is disposed than a cross-sectional area in a region where the guide portion is not disposed.

In another variant, the light source unit is disposed above the guide portion to face the photocatalyst filter.

In another variant, the first cross-sectional area is larger than the second cross-sectional area and the first flow speed is less than the second flow speed.

In another variant, a distance between the light source unit and the photocatalyst filter ranges from about 15 mm to about 25 mm.

In another variant, the first cross-sectional area is less than the second cross-sectional area and the first flow speed is greater than the second flow speed.

In another variant, the effective deodorization efficiency corresponds to a pollutant removal efficiency of 60% or more by the photocatalyst filter.

In another variant, the flow channel includes a first region including an inlet of the flow channel and having a cross-sectional area varying in the first direction; a second region disposed adjacent to the first region and having a constant cross-sectional area; and a third region including an outlet of the flow channel and having a cross-sectional area varying in the first direction.

In another variant, the first region of the flow channel has a cross-sectional area gradually decreasing in the first direction and the second region of the flow channel has the same cross-sectional area as the second cross-section.

In another variant, the photocatalyst filter is disposed in the second region.

In another variant, the absorption filter is disposed in the first region or in the third region.

In another variant, the fluid processing module further includes: a fan disposed in the flow channel of the main body.

In another variant, the photocatalyst filter extends in the first direction.

In another variant, light emitted from the light source unit includes light in the wavelength band of 315 nm to 400 nm.

In another variant, the light source unit includes multiple light sources and at least some of the multiple light sources emit light in different wavelength bands.

In another variant, at least some of the multiple light sources emit light having wavelengths in the wavelength band of 100 nm to 280 nm.

In another variant, a product of the first cross-sectional area and the first flow speed is the same as a product of the second cross-sectional area and the second flow speed.

In accordance with another aspect of the present disclosure, a storage device includes a casing having a storage space therein; and a fluid processing module disposed in a casing. The fluid processing module includes a main body having a flow channel extending in a first direction therein, an absorption filter disposed perpendicular to the first direction inside the main body, a photocatalyst filter disposed parallel to the first direction inside the main body; and a light source unit disposed inside the main body and emitting light towards the photocatalyst filter. The flow channel has a first cross-sectional area in a region where the absorption filter is disposed and a second cross-sectional area in a region where the photocatalyst filter is disposed. A fluid flows at a first flow speed in the region of the flow channel having the first cross-sectional area and at a second flow speed in the region of the flow channel having the second cross-sectional area. A product of the first cross-sectional area and the first flow speed is the same as a product of the second cross-sectional area and the second flow speed.

In another variant, the storage device further includes a fan circulating air inside the storage device, wherein the fan forces the air to flow towards the fluid processing module inside the storage device.

In another variant, the fluid processing module is provided in plural.

Embodiments of the present disclosure provide a fluid processing module having high efficiency in operation by preventing loss in flow speed upon fluid processing, such as deodorization, sterilization, and the like.

Embodiments of the present disclosure provide a fluid processing module capable of remarkably reducing power consumption through adjustment in flow speed of a fluid passing therethrough without using a fan such that a photocatalyst filter inside the fluid processing module has effective deodorization efficiency.

Embodiments of the present disclosure provide a fluid processing module having a compact structure and high utilization, and a storage device includes the fluid processing module occupying a narrow space, thereby securing a broad utilization space.

DETAILED DESCRIPTION OF EMBODIMENTS

Figure 1:
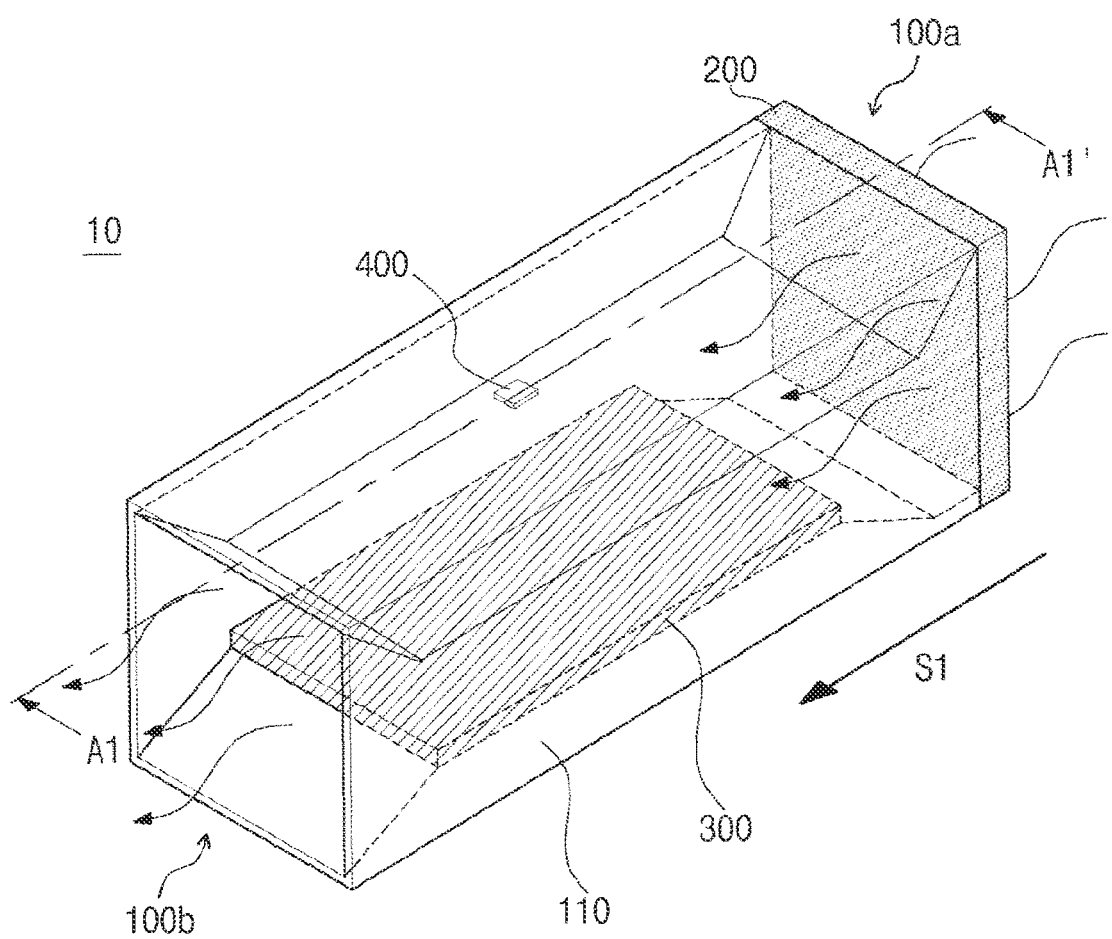
FIG. 1 is a perspective view of a fluid processing module according to one or more embodiments of the present disclosure.

The present disclosure may be realized by various embodiments and some exemplary embodiments of the present disclosure will be described in detail with reference to the accompanying drawings. However, it should be understood that the present disclosure is not limited to the following embodiments, and that various modifications, substitutions, and equivalent embodiments can be made by those skilled in the art without departing from the spirit and scope of the present disclosure.

Like components will be denoted by like reference numerals throughout the specification. It should be noted that the drawings may be exaggerated in thickness of lines or size of components for descriptive convenience and clarity only. It will be understood that, although the terms "first", "second", and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element or component discussed below could also be termed a "second" element or component, or vice versa, without departing from the scope of the present disclosure. As used herein, the singular forms "a" and "an" are intended to include the plural forms as well, unless the context clearly indicates otherwise.

It will be understood that the terms "includes", "comprises", "including" and/or "comprising," when used in this specification, specify the presence of stated features, steps, operations, elements, and/or components, but do not preclude the presence or addition of one or more other features, steps, operations, elements, components, and/or groups. It will be understood that, when an element, such as a layer, a film, a region, or a substrate, is referred to as being placed "on" another element, it can be directly placed on the other element, or intervening layer(s) may also be present. In addition, spatially relative terms, such as "upper" and "lower", are defined from the observer's point of view, and, when the observer's point of view is changed, "upper (portion)" may mean "lower (portion)", or vice versa. In addition, when an element, such as a layer, a film, a region, or a substrate, is referred to as being formed "on" another element, a direction in which the element is formed on the other element is not limited to an upward direction and includes a lateral direction or a downward direction. On the contrary, when an element, such as a layer, a film, a region, or a substrate, is referred to as being placed "under" another element, it can be directly placed under the other element, or intervening layer(s) may also be present.

Hereinafter, embodiments of the present disclosure will be described in detail with reference to the accompanying drawings.

One embodiment of the present disclosure provides a fluid processing module having a compact structure to secure high utilization and having high processing efficiency by preventing loss in flow speed upon fluid processing, such as deodorization, sterilization, and the like.

Herein, a fluid processed by the fluid processing module may have a gas phase. In addition, fluid processing refers to physical and/or chemical treatment of pollutants suspended in a fluid and includes sterilization through absorption and/or photocatalytic reaction.

Figure 2:
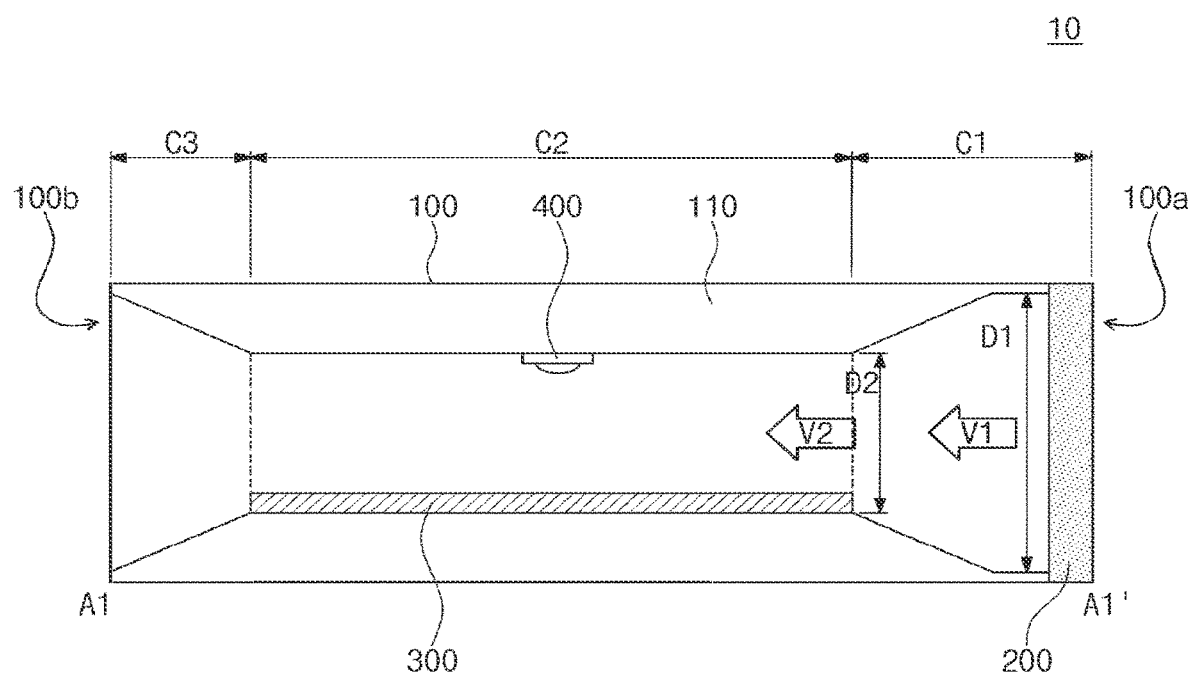
FIG. 2 is a cross-sectional view of the fluid processing module taken along line A1-A1' of FIG. 1.

FIG. 1 is a perspective view of a fluid processing module according to an embodiment of the present disclosure and FIG. 2 is a cross-sectional view of the fluid processing module taken along line A1-A1' of FIG. 1.

Referring to FIG. 1 and FIG. 2, the fluid processing module 10 according to the embodiment includes a main body 100, an absorption filter 200, a photocatalyst filter 300, and a light source unit 400.

The main body 100 defines an external appearance of the fluid processing module 10 and includes a flow channel along which a fluid flows. Specifically, the main body 100 has a main body inlet 100a through which the fluid enters the fluid processing module 10 and a main body outlet 100b through which the fluid is discharged from the fluid processing module 10 after being processed in the fluid processing module 10. The main body inlet 100a is connected to the main body outlet 100b through the flow channel defined in the main body 100.

The main body 100 extends between the main body inlet 100a and the main body outlet 100b in one direction. For example, the main body 100 may have an elongated shape extending in a first direction S1. For example, the main body 100 may have various shapes extending in one direction, such as a rectangular parallelepiped shape, a cylindrical shape, a triangular column shape, and the like. Like the main body 100, the flow channel may have an elongated shape extending in the first direction S1. The fluid having entered the fluid processing module 10 will be processed therein while flowing along the flow channel in the first direction S1.

The main body 100 may be formed of a material having high rigidity and low reactivity. For example, the main body 100 may be formed of at least one selected from the group consisting of polyethylene, polypropylene, polyvinylchloride, polystyrene, ABS (acrylonitrile-butadiene-styrene) resin, methacrylate resin, polyamide, polycarbonate, polyacetyl, polyethylene terephthalate, modified polyphenylene oxide, polybutylene terephthalate, polyurethane, phenolic resin, urea resin, melamine resin, or combinations thereof.

The main body 100 is provided with a guide portion 110. The guide portion 110 is formed inside the main body 100 to define the flow channel together with the main body 100. For example, the guide portion 110 may protrude from one inner surface of the main body 100, whereby the flow channel in a region where the guide portion 110 is disposed may have a narrower cross-sectional area than the flow channel in a region where the guide portion 110 is not disposed, as taken perpendicular to the first direction (the area of a cross-section of the flow channel perpendicular to the first direction S1 will be referred to as "cross-sectional area of the flow channel").

As the guide portion 110 defines the shape of the flow channel, as described above, the fluid flowing in the main body 100 may have a different flow speed at a certain location in the flow channel than flow speeds at other locations therein. Specifically, the flow channel in the region where the guide portion 110 is disposed may have a narrower cross-sectional area than the flow channel in the region where the guide portion 110 is not disposed. Accordingly, the flow channel in the region where the guide portion 110 is disposed may have a greater flow speed than the flow channel in the region where the guide portion 110 is not disposed.

The shape of the guide portion 110 may be determined so as to allow the most efficient deodorization and sterilization of the fluid processing module 10 through variation of the flow speed in the flow channel. For example, deodorization and sterilization of the fluid by the photocatalyst filter 300 can become most efficient when the fluid flows at a flow speed in a particular range, and the guide portion 110 may determine the flow speed of the fluid such that deodorization and sterilization of the fluid by the photocatalyst filter 300 can become the most efficient.

As shown in FIG. 1 and FIG. 2, the guide portion 110 decreases the width of the flow channel in the region where the photocatalyst filter 300 is disposed, whereby the fluid in the region where the photocatalyst filter 300 is disposed has a greater flow speed than the fluid in the main body inlet 100a or in the main body outlet 100b. Accordingly, even when the fluid flows at a relatively low flow speed in the main body inlet 100a, the flow speed of the fluid increases near the photocatalyst filter 300, thereby maximizing efficiency in deodorization and sterilization of the fluid by the photocatalyst filter 300.

Next, variation in flow speed and cross-sectional area of the flow channel by the guide portion 110 will be described in detail.

The guide portion 110 may be integrally formed with the main body 100 or may be separably provided to the main body 100. For example, the guide portion 110 may be detachably coupled to the main body 100. The guide portion 110 may be separated from or coupled to the main body 100, as needed. Accordingly, a user may suitably provide the guide portion 110 to the main body 100 depending upon the flow speed of the fluid entering the fluid processing module 10 so as to achieve most efficient deodorization and sterilization of the fluid inside the fluid processing module 10.

The main body 100 and the guide portion 110 are main components affecting flow of the fluid in the fluid processing module 10. The absorption filter 200 and the photocatalyst filter 300 described hereinafter are components for deodorization and sterilization of the fluid in the fluid processing module 10.

First, the absorption filter 200 removes foreign substances floating in the fluid flowing in the fluid processing module 10 through absorption. Accordingly, the absorption filter 200 may include various materials capable of adsorbing foreign substances, for example, activated carbon, glass fibers, polyesters, polypropylene, synthetic fibers including Nylon, acryl, and the like, and foamable materials including polyurethane, zeolite, alumina, silica, and the like.

The absorption filter 200 may remove floating substances from the fluid through physical, electrical or chemical absorption. For example, the absorption filter 200 may attract the floating substances in the fluid using electrostatic force by applying an electric field to the flow channel. Alternatively, the absorption filter 200 may use chemisorption reaction to remove a toxic gas from the fluid. For example, the absorption filter 200 may be provided with a mixture of activated carbon and sodium hydroxide (NaOH) or potassium hydroxide (KOH) to remove not only a floating substance, such as dust and the like, but also a toxic gas. It should be understood that the above structure is provided by way of example of the absorption filter 200 and various kinds of filters may be used as the absorption filter 200, as needed. For example, a HEPA filter, a ULPA filter, a SULPA filter, and the like may be used as the absorption filter 200.

The absorption filter 200 may be provided to the main body inlet 100a and/or the main body outlet 100b in the main body 100. The absorption filter 200 may be disposed singularly or in plural in consideration of the length of the main body 100 and an average flow speed of the fluid flowing into the main body 100.

The absorption filter 200 may have a shape corresponding to the shape of the main body 100 or to the shapes of the main body inlet 100a and the main body outlet 100b. For example, when the absorption filter 200 is provided to the main body inlet 100a, the main body inlet 100a may have a shape corresponding to the shape of the absorption filter 200. Accordingly, the absorption filter 200 may be disposed to closely contact the main body inlet 100a.

The absorption filter 200 may be disposed substantially perpendicular to the first direction S1 in which the main body 100 or the flow channel extends. Here, the structure of the absorption filter 200 disposed substantially perpendicular to the first direction S1 includes not only a structure in which the absorption filter 200 is completely perpendicular to the first direction S1, but also a structure in which an angle defined between the absorption filter 200 and the first direction S1 approaches 90 degrees, or a structure in which a tangential line on a curved surface of the absorption filter 200 having a curved shape is perpendicular to the first direction S1. With the structure of the absorption filter 200 disposed substantially perpendicular to the first direction S1 in which the main body 100 or the flow channel extends, the fluid can flow in a direction perpendicular to the absorption filter 200 while passing through the fluid processing module 10. As a result, floating substances can be efficiently removed from the fluid by the absorption filter 200.

In some forms, the absorption filter 200 may include multiple pores. The multiple pores in the absorption filter 200 increase a contact area between the fluid and the absorption filter 200. As a result, absorption of the floating substances in the fluid by the absorption filter 200 can be more actively performed. In this case, the size and the number of pores in the absorption filter 200 may be determined so as not to provide significant restriction on the flow speed of the fluid entering the fluid processing module 10.

The absorption filter 200 physically removes the floating substances from the fluid through absorption, whereas the photocatalyst filter 300 removes pollutants from the fluid mainly through chemical reaction.

The photocatalyst filter 300 performs photocatalytic reaction with light emitted from the light source unit 400. The fluid flowing through a region in which the photocatalyst filter 300 is disposed is deodorized and sterilized by photocatalytic reaction.

Photocatalytic reaction performed by the photocatalyst filter 300 may be a reaction by which superoxide anions ($O^{2-}$) and/or hydroxyl radicals (OH·) are generated from water and oxygen in air. The superoxide anions ($O^{2-}$) and/or the hydroxyl radicals (OH·) can decompose or disinfect organic and inorganic pollutants, viruses, and bacteria. Specifically, the organic pollutants may be decomposed into water and carbon dioxide through reaction with the superoxide anions ($O^{2-}$) and/or the hydroxyl radicals (OH·). The organic pollutants may be decomposed into oxides, such as nitrogen oxide and the like. Viruses or bacteria can be inactivated through reaction with the superoxide anions ($O^{2-}$) and/or the hydroxyl radicals (OH·). Specifically, the superoxide anions ($O^{2-}$) and/or the hydroxyl radicals (OH·) inactivate the viruses or the bacteria through reaction with DNA and cell membranes of the viruses or the bacteria.

For photocatalytic reaction, the photocatalyst filter 300 may include a photocatalytic material on at least a surface thereof irradiated with light. The photocatalytic material may include at least one selected from among titanium dioxide ($TiO_2$), zirconia ($ZrO_2$), zinc oxide (ZnO), tungsten oxide ($WO_3$), zinc oxide (ZnO), and tin oxide ($SnO_2$). In one embodiment, since there is a limit in use of holes and electrons generated from a surface of a photocatalyst for photochemical reaction due to a very high recombination rate of the holes and the electrons, the photocatalytic material may contain metals, such as Pt, Ni, Mn, Ag, W, Cr, Mo, Zn, and the like, or oxides thereof to retard the recombination rate of the holes and the electrons. When the recombination rate of the holes and the electrons is retarded, reactivity can be increased through increase in possibility of contact between the photocatalytic material and a target material to be oxidized and/or decomposed. Furthermore, it is also possible to improve performance of the photocatalyst filter 300 by adjusting a photocatalyst band-gap by adding an oxide to the photocatalytic material. By the aforementioned photocatalytic reaction, air can be sterilized, purified, and deodorized. In particular, the photocatalyst filter can prevent growth of viruses or fungi and can decompose toxins released from the viruses or the fungi through sterilization or antibacterial reaction by which enzymes in the cells of the viruses and enzymes acting on the respiratory system thereof are destroyed.

The photocatalyst filter 300 may include a matrix or beads coated with the aforementioned photocatalytic materials. The matrix or beads of the photocatalyst filter 300 may include at least one selected from among alumina ($Al_2O_3$), silicon oxide ($SiO_2$), zirconia ($ZrO_2$), silicon nitride ($Si_3N_4$), silicon carbide (SiC), and combinations thereof.

The photocatalyst filter 300 may be disposed inside the main body 100. For example, the photocatalyst filter 300 may be disposed inside the flow channel in the main body 100. Accordingly, in the fluid processing module 10, the fluid may meet the photocatalyst filter 300 in at least some regions of the flow channel. As photocatalytic reaction occurs in the photocatalyst filter 300, the fluid is deodorized and sterilized by photocatalytic reaction while passing through the photocatalyst filter 300.

According to the embodiment, the photocatalyst filter 300 is disposed on the guide portion 110. When the photocatalyst filter 300 is disposed on the guide portion 110, the flow channel in a region where the photocatalyst filter 300 is disposed has a smaller cross-sectional area than the flow channel in other regions, as measured perpendicular to the first direction S1. Accordingly, the superoxide anions ($O^{2-}$) and/or the hydroxyl radicals (OH·) generated from the surface of the photocatalyst filter 300 through photocatalytic reaction can be easily diffused to a region away from the photocatalyst filter 300. As a result, deodorization and sterilization may be uniformly performed not only through the fluid flowing on the photocatalyst filter 300, but also on the fluid flowing above the photocatalyst filter 300.

The photocatalyst filter 300 may be disposed such that an upper surface thereof is parallel to the first direction S1 in which the main body 100 or the flow channel extends. Here, the structure of the photocatalyst filter 300 disposed parallel to the first direction S1 includes a structure of the photocatalyst filter 300 disposed substantially parallel to the first direction S1. Since the photocatalyst filter 300 is disposed substantially parallel to the first direction S1 in which the main body 100 or the flow channel extends, the fluid can flow along the surface of the photocatalyst filter 300 in at least some regions inside the fluid processing module 10. As a result, deodorization and sterilization can be uniformly performed not only through the fluid flowing on the photocatalyst filter 300, but also on the fluid flowing above the photocatalyst filter 300.

As the photocatalyst filter 300 is disposed parallel to the first direction S1, there is no concern that the photocatalyst filter 300 obstructs the flow of the fluid in the flow channel. Accordingly, it is possible to increase the size of the photocatalyst filter 300 and to improve photocatalytic reaction without obstructing the flow of the fluid. Thus, the fluid processing module 10 according to the embodiment can realize a compact structure while increasing the size of the photocatalyst filter 300.

To activate photocatalytic reaction in the photocatalyst filter 300, the light source unit 400 emits light to the photocatalyst filter 300.

Specifically, the light source unit 400 is spaced apart from the photocatalyst filter 300 and emits light towards the photocatalyst filter 300. Light emitted from the light source unit 400 may be light in a wavelength band capable of activating photocatalytic reaction on the photocatalyst filter 300. Specifically, the light emitted from the light source unit 400 may be light in the UV wavelength band or in other wavelength bands including the visible spectrum. The light emitted from the light source unit 400 and in the above wavelength band can activate a particular kind of photocatalytic material.

The light emitted from the light source unit 400 may be, for example, light in the UV wavelength band. Specifically, the light emitted from the light source unit 400 may be light in the UV-A wavelength band (from about 315 nm to about 400 nm). The light emitted from the light source unit 400 and in the UV-A wavelength band can effectively activate a particular kind of photocatalytic material in the photocatalyst filter 300.

The light emitted from the light source unit 400 may include light in wavelength bands other than light in the UV-A wavelength band. For example, the light emitted from the light source unit 400 may be UV-C light (in the wavelength band of about 100 nm to about 280 nm), UV-C light (in the UV-B wavelength band of about 280 nm to about 315 nm), or visible light in the wavelength band of about 400 nm to about 430 nm. The light in the aforementioned wavelength bands may be emitted to the photocatalyst filter 300 to assist in activation of the photocatalytic material or may be emitted to pollutants in the fluid flowing in the fluid processing module 10 to directly remove the pollutants. Among the light in the aforementioned wavelength bands, the light in the UV-C wavelength band has high intensity to easily destroy bacteria, viruses, DNA, protein, and the like. In particular, since visible light in the wavelength band of about 400 nm to about 430 nm can be observed through the naked eye, the visible light is emitted together with light in the UV wavelength band to allow a user to visibly monitor whether the fluid processing module 10 is operated.

In some forms, the light source unit 400 includes a light source, a substrate, and a power source. The light source and the substrate may be disposed inside the fluid processing module 10. The power source may be connected to an external power source or may be embedded in the form of a battery inside the fluid processing module 10 to supply electric power to the light source unit 400.

The substrate of the light source unit 400 supports the light source and may be disposed on the main body 100. Specifically, when the light source is disposed on the main body 100 or the guide portion 110 defining the flow channel, the substrate may also be disposed on the main body 100 or the guide portion 110. However, the substrate may be omitted depending upon the type of light source.

The light source of the light source unit 400 emits light and may be disposed to face the photocatalyst filter 300. Accordingly, most light emitted from the light source is directed to the photocatalyst filter 300. As a result, photocatalytic reaction can be effectively activated on the photocatalyst filter 300. Since the photocatalyst filter 300 can be directly irradiated with most light emitted from the light source unit 400, photocatalytic reaction efficiency can be improved even with a small number of light sources. Accordingly, the fluid processing module 10 may reduce the number of light sources, thereby enabling reduction in power consumption.

As described above, the light source of the light source unit 400 may emit light in various wavelength bands. For example, the light source may emit light in the UV wavelength band. The light source may include, for example, a light emitting diode (LED).

The light source unit 400 may include multiple light sources. The light sources of the light source unit 400 may be arranged in consideration of the shape and location of the photocatalyst filter 300. For example, in the structure in which the photocatalyst filter 300 extends in the first direction S1, the multiple light sources may be separated from each other in the first direction S1. This structure maximizes a region of the photocatalyst filter 300 in which photocatalytic reaction is activated.

In the light source unit 400 including the multiple light sources, the multiple light sources may emit light in the same wavelength band or light in different wavelength bands. For example, each of the light sources may emit light in the UV wavelength band. Alternatively, some light sources may emit light in some regions of the UV wavelength band and the other light sources may emit light in the other regions of the UV wavelength band. By way of example, some light sources may emit light in the UV-A wavelength band (in the wavelength range of about 320 nm to about 400 nm) to activate the photocatalytic material and the other light sources may emit light having different wavelengths than the light in the UV-A wavelength band. In particular, the light emitted from the other light sources may include light in the UV-C wavelength band (in the wavelength range of about 100 nm to about 280 nm), which can directly sterilize and remove floating pollutants in the fluid. Some light sources may emit light in the wavelength band of about 400 nm to about 430 nm to sterilize and remove the floating pollutants in the fluid while allowing a user to monitor whether the light source unit 400 is operated. Here, the light sources emitting light in different wavelength bands may be independently operated. As a result, the light source unit 400 emits light in a suitable wavelength band according to user manipulation or a preset algorithm in the controller.

As shown in FIG. 1 and FIG. 2, the light source of the light source unit 400 may be disposed above the guide portion 110 when the photocatalyst filter 300 is disposed on the guide portion 110. Here, the flow channel defined by the guide portion 110 has a narrower cross-sectional area than the flow channel in a region where the guide portion 110 is not disposed, whereby the light source can be disposed relatively close to the photocatalyst filter 300. For example, the distance between the light source (or the light source unit 400) and the photocatalyst filter 300 may range from about 15 mm to about 25 mm. Within this range, the light emitted from the light source can maximize photocatalytic reaction activity on the photocatalyst filter 300.

In the above description, each of the components of the fluid processing module 10 for deodorization and sterilization of the fluid is described. The following description will focus on flow of the fluid in the fluid processing module 10 and functions of the components described above.

According to one embodiment, the flow channel includes a first region C1 including the main body inlet 100*a* and having a cross-sectional area varying in the first direction S1, a second region C2 disposed adjacent to the first region C1 and having a constant cross-sectional area, and a third region C3 including the main body outlet 100b and having a cross-sectional area varying in the first direction S1, as shown in FIG. 2.

The first region C1, the second region C2, and the third region C3 may be sequentially arranged. As can be seen from FIG. 1 and FIG. 2, the flow channel in the first region C1 may have a cross-sectional area gradually decreasing in the first direction S1 and the flow channel in the third region C3 may have a cross-sectional area gradually increasing in the first direction S1. Accordingly, in the first region C1 to the third region C3, the flow channel may have a shape having a cross-sectional area, which is gradually narrowed, converged to a constant value, and is then gradually increased, as shown in FIG. 2.

The first region C1 and/or the third region C3 may be provided with the absorption filter 200 and the second region C2 may be provided with the photocatalyst filter 300. As described above, the photocatalyst filter 300 disposed in the second region C2 may have an elongated shape extending in the first direction S1. The photocatalyst filter 300 may have the same length as or a smaller length than the second region C2.

In the first region C1 and the third region C3, the flow channel has a cross-sectional area larger than or equal to the cross-sectional area of the flow channel in the second region C2. Specifically, in the first region C1 and the third region C3, the minimum cross-sectional area of the flow channel may be substantially the same as the cross-sectional area of the flow channel in the second region C2. In description of the cross-sectional area of the second region C2, description of a cross-sectional area of the photocatalyst filter 300 taken in a thickness direction thereof will be omitted. As compared with the cross-sectional area of the flow channel, the cross-sectional area of the photocatalyst filter 300 is small and thus provides insignificant influence on the flow of the fluid.

When the cross-sectional area of the flow channel in the first region C1 and the third region C3 is larger than the cross-sectional area of the flow channel in the second region C2, the flow speed in the first region C1 and the third region C3 may be less than the flow speed in the second region C2. Here, the flow speed in each region may refer to an average value of flow speeds in various points in each region. As described above, in the structure in which the absorption filter 200 is disposed in the first region C1 and the photocatalyst filter 300 is disposed in the second region C2, a first cross-sectional area D1 corresponding to the cross-sectional area of the flow channel in the region where the absorption filter 200 is disposed may be larger than a second cross-sectional area D2 corresponding to the cross-sectional area of the flow channel in the region where the photocatalyst filter 300 is disposed. As a result, a first flow speed V1 corresponding to the flow speed of the fluid flowing in the flow channel having the first cross-sectional area D1 may be less than a second flow speed V2 corresponding to the flow speed of the fluid flowing in the flow channel having the second cross-sectional area D2.

In the above example, a product of the first flow speed V1 and the first cross-sectional area D1 may be substantially the same as a product of the second flow speed V2 and the second cross-sectional area D2.

When the fluid flows as described above, the fluid in the first region C1, where the absorption filter 200 is disposed, flows more slowly than the fluid in the second region C2 where the photocatalyst filter 300 is disposed. As a result, it is possible to adjust the flow speed of the fluid flowing in the second region C2 such that the photocatalyst filter 300 has effective deodorization efficiency.

By adjusting the flow speed of the fluid in the second region C2 where the photocatalyst filter 300 is disposed, the photocatalyst filter 300 can have effective deodorization efficiency.

Specifically, when the flow speed of the fluid passing through the photocatalyst filter 300 is within an effective range, the photocatalyst filter 300 can exhibit effective deodorization efficiency. If the flow speed of the fluid in the photocatalyst filter 300 is less than the effective range, the amount of the fluid per hour subjected to deodorization, sterilization in the photocatalyst filter 300 can be excessively reduced, thereby deteriorating efficiency in deodorization and sterilization of the fluid. On the other hand, if the flow speed of the fluid in the photocatalyst filter 300 exceeds the effective range, the fluid passes through the photocatalyst filter 300 before deodorization and sterilization of the fluid through photocatalytic reaction in the photocatalyst filter 300, thereby deteriorating efficiency in deodorization and sterilization of the fluid. Accordingly, when the flow speed of the fluid is within the effective range, the photocatalyst filter 300 can have effective deodorization efficiency.

By way of example only, the effective deodorization efficiency may be about 60%. If the deodorization efficiency is less than 60%, viruses and bacteria can be actively propagated, thereby providing insignificant effects in deodorization and sterilization.

In the fluid processing module 10 according to the embodiment, the shape of the flow channel may be determined such that the fluid passing through the photocatalyst filter 300 has a flow speed within the effective range. For example, if the flow speed of the fluid entering the fluid processing module 10 is less than the effective range, the flow channel of the fluid processing module 10 is designed such that the second flow speed V2 in the second region C2 where the photocatalyst filter 300 is disposed is greater than the first flow speed V1 in the first region C1 through which the fluid enters the fluid processing module 10. Specifically, the guide portion 110 is provided to the fluid processing module 10 such that the cross-sectional area of the flow channel D2 in the second region C2 is less than the cross-sectional area of the flow channel D1 in the first region C1.

With the guide portion 110 described above, the fluid processing module 10 allows the fluid to flow at a flow speed within the effective range in the photocatalyst filter 300, regardless of the flow speed of the fluid entering the fluid processing module 10. As a result, the photocatalyst filter 300 can exhibit effective deodorization efficiency.

In particular, according to the embodiment, the fluid processing module 10 can control the flow speed of the fluid in the photocatalyst filter 300 to be within the effective range without a fan for controlling the flow speed of the fluid entering the fluid processing module 10. Accordingly, the fluid processing module 10 according to the embodiment can be driven without electric power for operation of the fan, thereby securing effective deodorization efficiency even with very low electric power. As a result, the fluid processing module 10 has very high fluid processing efficiency, as compared with consumed power. Further, since the size of the fan is not taken into account in design of the fluid processing module 10 by omitting the fan, the fluid processing module can be manufactured to have a more compact structure. Accordingly, the fluid processing module 10 can be installed in a narrow space, thereby securing very high space utilization.

In the above description, the fluid processing module 10 including the flow channel having various cross-sectional areas according to regions of the flow channel is described.

According to the embodiment, since the fluid processing module 10 is provided with the photocatalyst filter 300 so as not to obstruct the flow of the fluid, the processing amount of the fluid per hour can be increased. Further, the flow speed of the fluid in the photocatalyst filter 300 may be adjusted using the guide portion 110 such that the photocatalyst filter 300 can have effective deodorization efficiency. Furthermore, the fluid processing module 10 allows the flow speed of the fluid to be within the effective range without the fan for adjusting the flow speed of the fluid, thereby securing very high fluid processing efficiency, as compared with consumed power thereof.

It should be understood that the guide portion 110 may be modified in various ways so long as the guide portion 110 allows the photocatalyst filter 300 to have effective deodorization efficiency. The following description will focus on modified structures of the guide portion 110.

Figure 3:
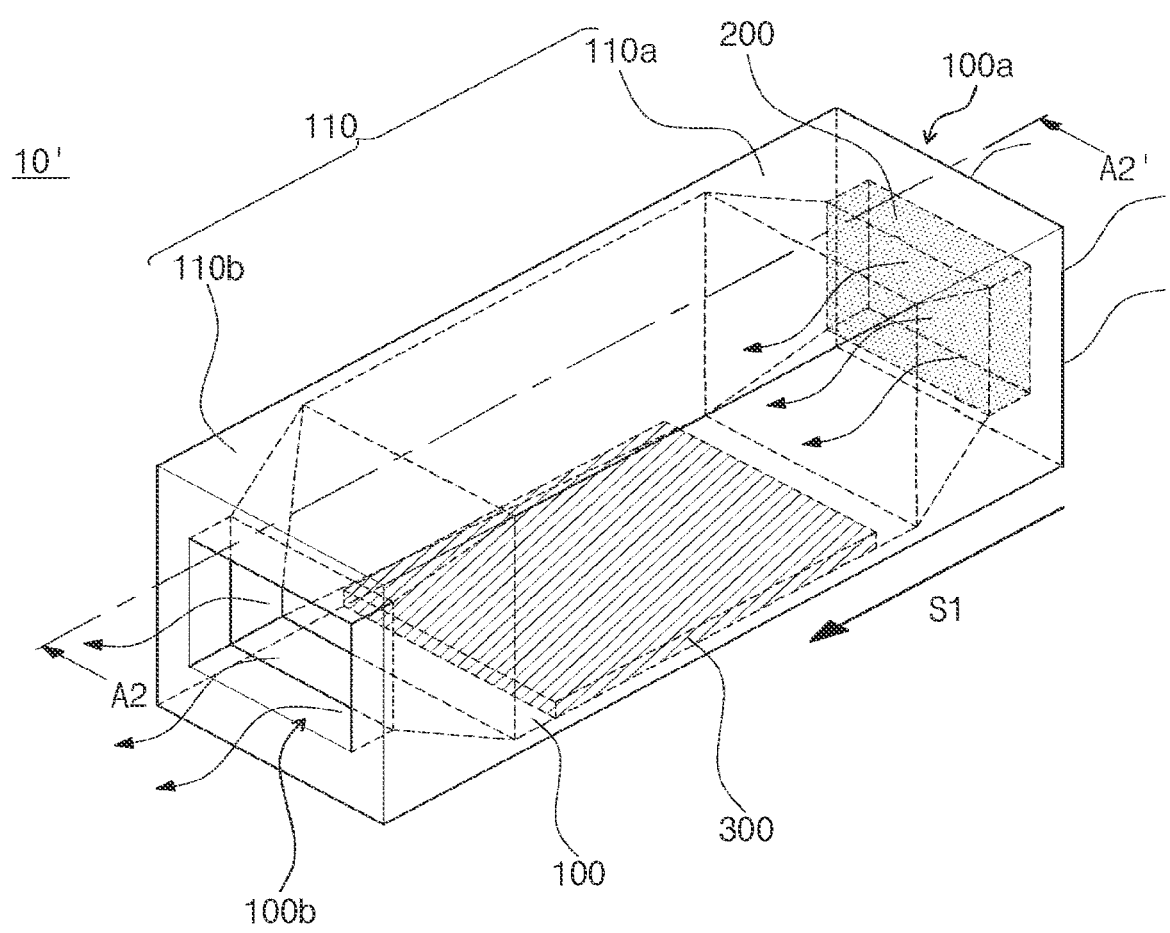
FIG. 3 is a perspective view of a fluid processing module according to another embodiment of the present disclosure.
Figure 4:
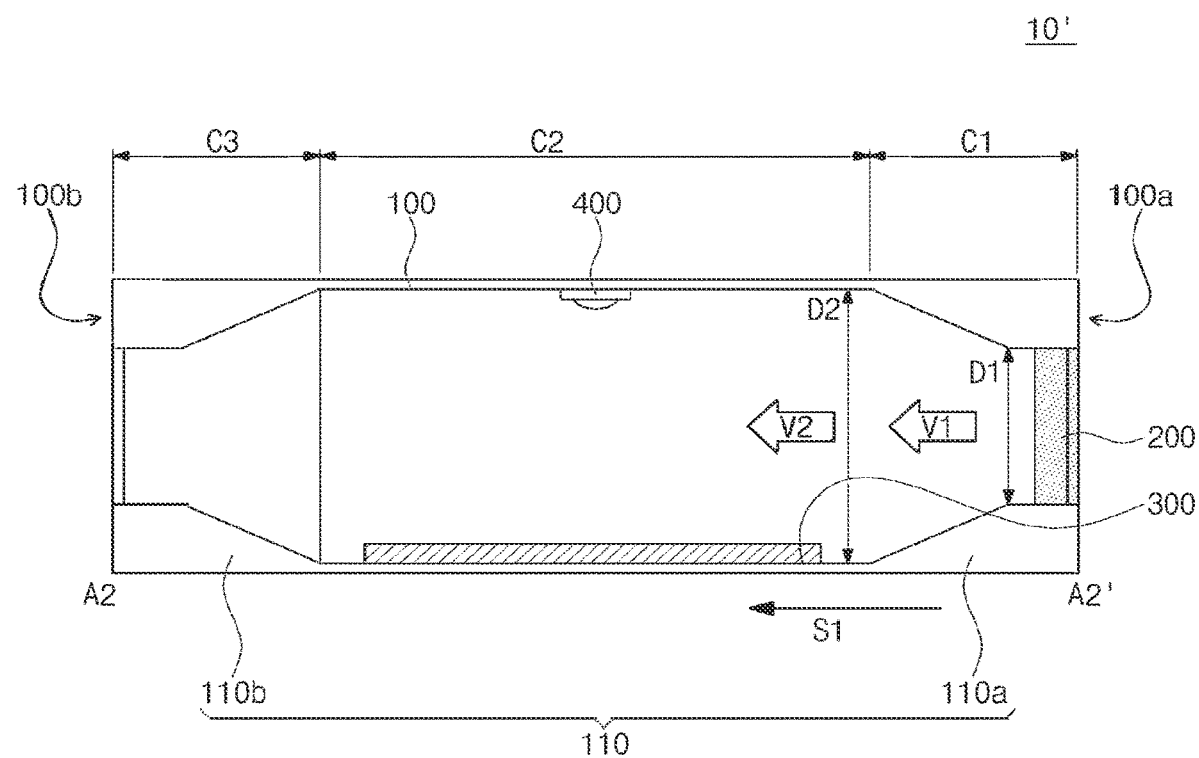
FIG. 4 is a cross-sectional view of the fluid processing module taken along line A2-A2' of FIG. 3.

FIG. 3 is a perspective view of a fluid processing module according to another embodiment of the present disclosure and FIG. 4 is a cross-sectional view of the fluid processing module taken along line A2-A2' of FIG. 3.

Referring to FIG. 3 and FIG. 4, a fluid processing module 10' includes a main body 100, an absorption filter 200, a photocatalyst filter 300, and a light source unit 400. Description of the same components of the fluid processing module shown in FIG. 3 and FIG. 4 as those of the fluid processing module described above with reference to FIG. 1 and FIG. 2 will be omitted to avoid repetition.

The flow channel defined in the fluid processing module 10' includes a first region C1 including the main body inlet 100a and having a cross-sectional area varying in the first direction S1, a second region C2 disposed adjacent to the first region C1 and having a constant cross-sectional area, and a third region C3 including the main body outlet 100b and having a cross-sectional area varying in the first direction S1.

The guide portion 110 may range from the first region C1 to the third region C3. Here, the guide portion 110 provided to one region may have a different shape from the guide portion 110 provided to other regions. For example, the guide portion 110 provided to the first region C1 and the third region C3 has an inclined surface and a relatively great thickness. On the other hand, the guide portion 110 provided to the second region C2 has no inclined surface and a relatively small thickness. Accordingly, in at least some zone of the first region C1, the flow channel may have a cross-sectional area gradually increasing in the first direction S1 and in at least some zone of the third region C3, the flow channel may have a cross-sectional area gradually decreasing in the first direction S1. In the second region C2, the flow channel may have a substantially constant cross-sectional area in the first direction S1.

Since the guide portion 110 is separately provided to the first region C1 and the third region C3, the guide portion 110 may include several sections separated from each other. For example, the guide portion 110 may include a guide leading end 110a provided to the first region C1 and a guide proximal end 110b provided to the third region C3. The guide leading end 110a and the guide proximal end 110b may be separated from each other and may have symmetrical shapes. In some embodiments, the guide portion 110 may be disposed only in some regions of the first region C1 and the third region C3.

The absorption filter 200 may be provided to the first region C1 and/or the third region C3 and may be coupled to the guide portion 110, as shown in the drawings. For example, as shown in FIG. 4, the absorption filter 200 may be fastened to the guide portion leading end 110a without a gap therebetween.

In this embodiment, in the first region C1 and the third region C3, the cross-sectional area of the flow channel may be less than or equal to the cross-sectional area of the flow channel in the second region C2. Specifically, in the first region C1 and the third region C3, the maximum cross-sectional area of the flow channel may be substantially the same as the cross-sectional area of the flow channel in the second region C2. In description of the cross-sectional area of the second region C2, the cross-sectional area of the photocatalyst filter 300 taken in the thickness direction thereof should be taken into account. This is because the cross-sectional area of the photocatalyst filter 300 is relatively small, as compared with the cross-sectional area of the flow channel.

When the cross-sectional area of the flow channel in each of the first region C1 and the third region C3 is less than or equal to the cross-sectional area of the flow channel in the second region C2, the flow speed in each of the first region C1 and the third region C3 may be greater than the flow speed in the second region C2. Here, the flow speed in each region may refer to an average value of flow speeds at various points in the corresponding region. As described above, in the structure in which the absorption filter 200 is disposed in the first region C1 and the photocatalyst filter 300 is disposed in the second region C2, a first cross-sectional area D1 corresponding to the cross-sectional area of the flow channel in the region where the absorption filter 200 is disposed may be less than a second cross-sectional area D2 corresponding to the cross-sectional area of the flow channel in the region where the photocatalyst filter 300 is disposed, as shown in FIG. 4. Further, a first flow speed V1 corresponding to the flow speed of the fluid flowing in the flow channel having the first cross-sectional area D1 may be greater than a second flow speed V2 corresponding to the flow speed of the fluid flowing in the flow channel having the second cross-sectional area D2.

When the fluid flows as described above, the fluid in the first region C1 where the absorption filter 200 is disposed may flow faster than the fluid in the second region C2 where the photocatalyst filter 300 is disposed. As a result, it is possible to adjust the flow speed of the fluid flowing in the second region C2 such that the photocatalyst filter 300 has effective deodorization efficiency.

Specifically, in the fluid processing module 10' according to the embodiment, the shape of the flow channel may be determined such that the fluid passing through the photocatalyst filter 300 has a flow speed within the effective range. For example, if the flow speed of the fluid entering the fluid processing module 10' is greater than the effective range, the flow channel of the fluid processing module 10' according to the embodiment is designed such that the second flow speed V2 in the second region C2 provided with the photocatalyst filter 300 is less than the first flow speed V1 in the first region C1 through which the fluid enters the fluid processing module 10. To this end, the guide portion 110 is provided to the fluid processing module 10 such that the cross-sectional area of the flow channel D2 in the second region C2 is greater than the cross-sectional area of the flow channel D1 in the first region C1.

With the guide portion 110 described above, the fluid processing module 10' allows the fluid to flow at a flow speed within the effective range in the photocatalyst filter 300, regardless of the flow speed of the fluid entering the fluid processing module 10. As a result, the photocatalyst filter 300 can exhibit effective deodorization efficiency.

The above description is focused on the components of the fluid processing module 10 for increasing or decreasing the flow speed in the photocatalyst filter 300 such that the photocatalyst filter 300 can have effective deodorization efficiency. Next, various modification of the fluid processing module 10 according to the embodiment of the present disclosure will be described.

Figure 5:
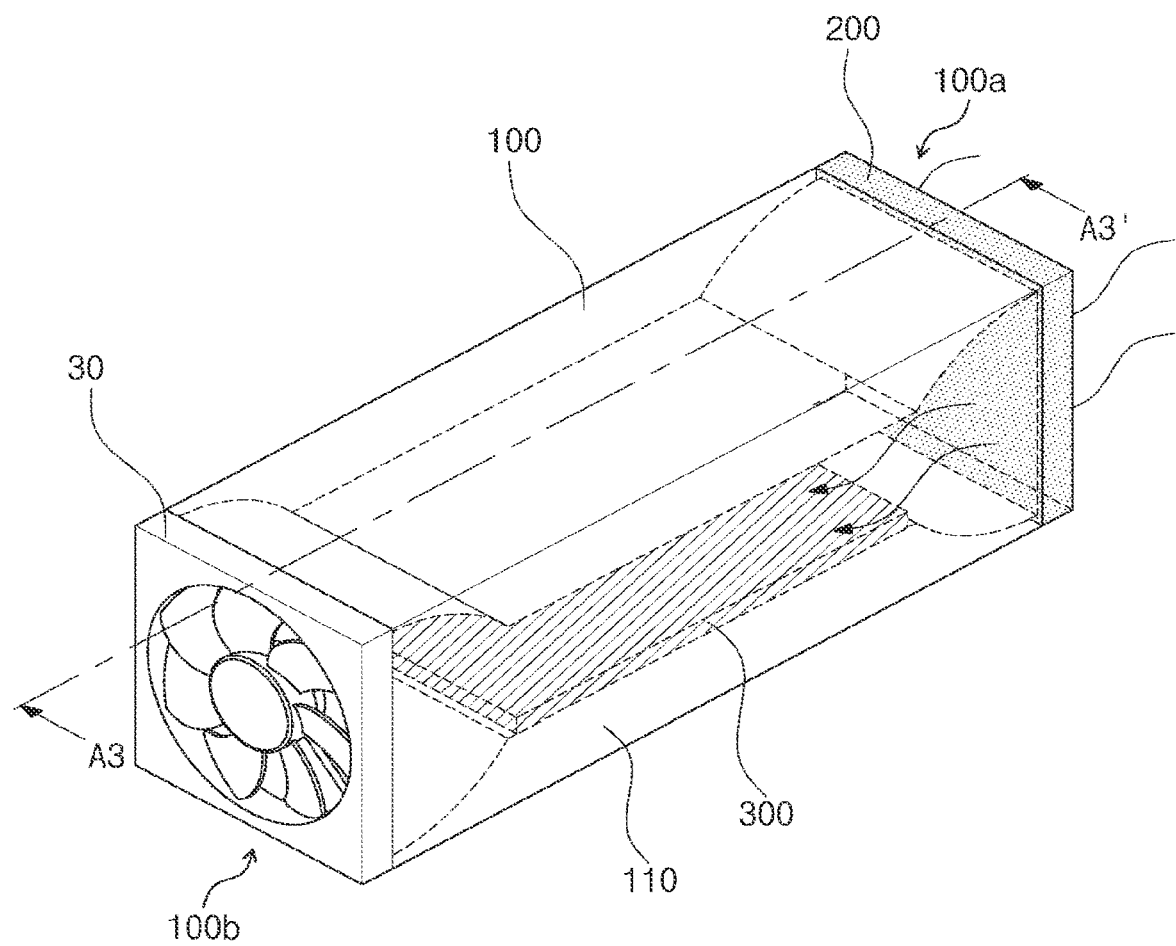
FIG. 5 is a perspective view of the fluid processing module according to a further embodiment of the present disclosure.
Figure 6:
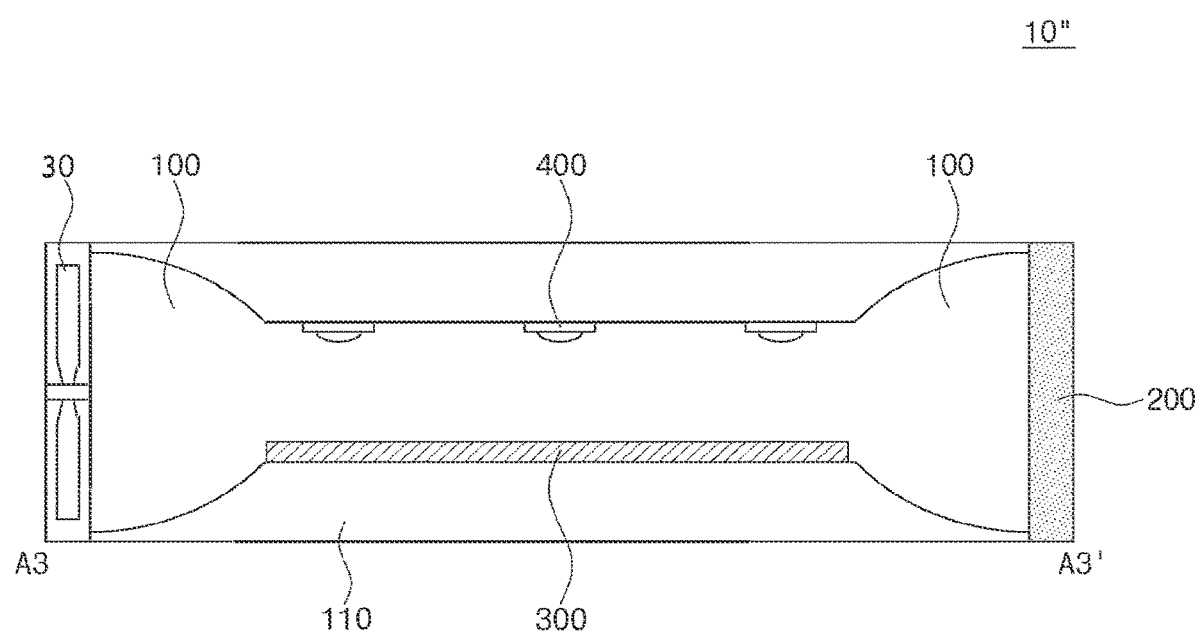
FIG. 6 is a cross-sectional view of the fluid processing module according to the embodiment of the present disclosure.
Figure 7A:
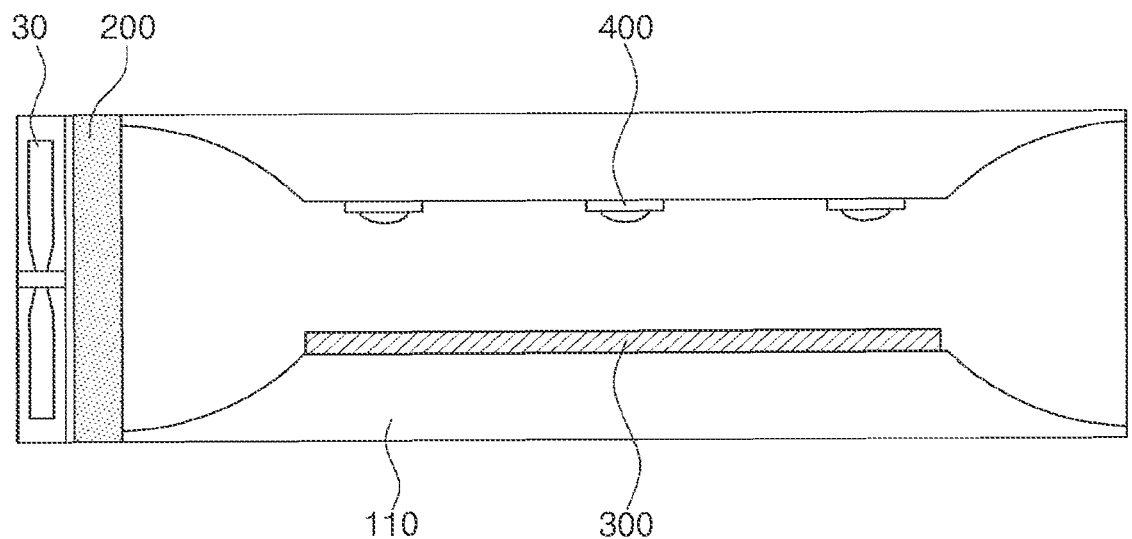
FIG. 7A is a cross-sectional view of the fluid processing module according to the embodiment of the present disclosure.
Figure 7B:
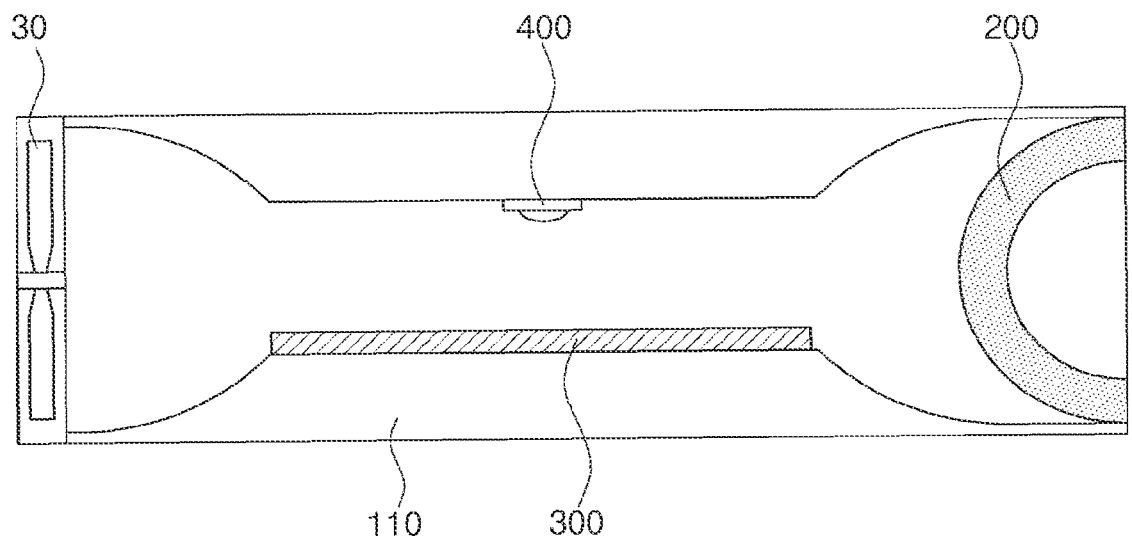
FIG. 7B is another cross-sectional view of the fluid processing module according to the embodiment of the present disclosure.

FIG. 5 is a perspective view of the fluid processing module according to a further embodiment of the present disclosure and FIG. 6 is a cross-sectional view of the fluid processing module taken along line A3-A3' of FIG. 5. FIG. 7A and FIG. 7B are cross-sectional views of the fluid processing module according to the embodiment of the present disclosure.

Referring to FIG. 5 and FIG. 6, a fluid processing module 10" includes a guide portion 110 having curved surfaces each having an inclination and facing a main body inlet 100a and a main body outlet 100b, respectively, and a fan provided to the main body outlet 100b.

The guide portion 110 has the curved surfaces each having an inclination, thereby minimizing vortex generation in the fluid having passed through the main body inlet and flowing towards the photocatalyst filter 300. As a result, the fluid processing module 10" does not obstruct the flow of the fluid and can improve efficiency in deodorization and sterilization of the fluid. Alternatively, only some inclined surfaces of the guide portion 110 may have a curved surface unlike the guide portion shown in the drawings.

The fan is provided to the main body outlet 100b or to the main body inlet 100a and assists in flow of the fluid through the fluid processing module 10". Specifically, a flow speed of the fluid flowing in the first direction can be increased by operation of the fan. Since the flow speed and flow rate of the fluid flowing through the fluid processing module 10" can vary according to operating intensity of the fan, the operating intensity of the fan may be adjusted such that the photocatalyst filter 300 exhibits effective deodorization efficiency.

There is no limit to the type of fan. For example, the fan may be selected from among various types of fans, such as a turbo fan, an airfoil fan, a radial fan, a sirocco fan, a once-through fan, a four-flow fan, an axial fan, a blower, and the like.

The fan may have substantially the same size as the main body outlet 100b or the main body inlet 100a. The fan may be closely coupled to the main body outlet 100b or the main body inlet 100a without a gap therebetween.

The fan and the absorption filter 200 may be disposed in the same region of the flow channel or in different regions thereof. For example, as shown in FIG. 7A, both the fan and the absorption filter 200 may be provided to the main body outlet side. In this case, although the flow speed can be decreased while the fluid passes through fine pores on the main body outlet, the fan can increase the flow speed. Accordingly, the size of the pores of the absorption filter 200 may be further reduced, thereby improving absorption efficiency through increase in contact area between the absorption filter 200 and the fluid.

When the fan and the absorption filter 200 are disposed in different regions of the flow channel, the absorption filter 200 may have various shapes. For example, as shown in FIG. 7B the absorption filter 200 may have a curved surface. In this structure, the contact area between the absorption filter 200 and the fluid can be increased without reduction in size of the pores, thereby improving absorption efficiency.

According to the present disclosure, the fan may be used as an assistant component. Specifically, the fluid processing module 10" according to this embodiment may control the fluid to flow at a flow rate within the effective range using the guide portion even without the fan. Accordingly, the fan provided to the fluid processing module 10" may be a fan adapted to consume relatively low electric power. Even with the fan adapted to consume low electric power, the fluid processing module 10" can achieve effective deodorization efficiency using a fan having a smaller size than that of a typical fluid processing module. Accordingly, the fluid processing module 10" can be designed regardless of the size of the fan, thereby providing a more compact structure.

As described above, according to embodiments of the present disclosure, various components may be provided to the fluid processing module and the components of the fluid processing module may be modified in various ways.

As described above, according to the embodiments, the photocatalyst filter can exhibit effective deodorization efficiency by adjusting the flow rate in the region of the flow channel provided with the photocatalyst filter using the guide portion. Next, effective deodorization efficiency will be described in more detail.

Figure 8:
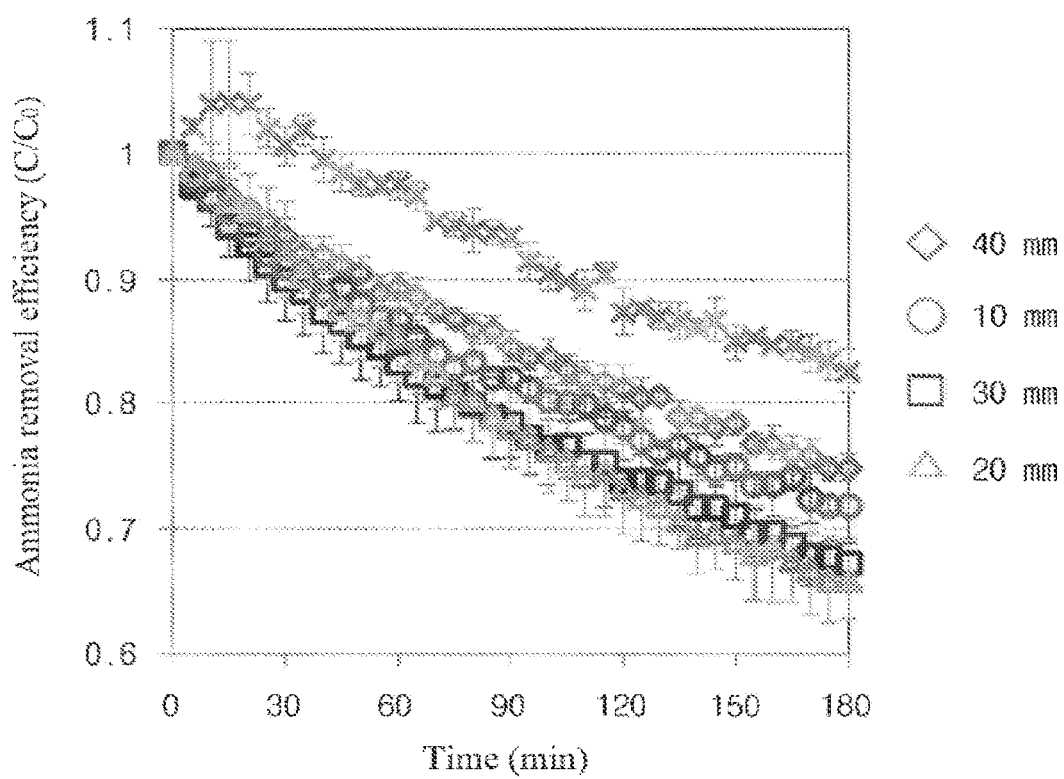
FIG. 8 is a graph depicting ammonia removal efficiency depending on a distance between a light source unit and a photocatalyst filter.

First, FIG. 8 is a graph depicting ammonia removal efficiency depending on the distance between the light source unit and the photocatalyst filter. To obtain data of the graph shown in FIG. 8, other parameters except for the distance between the light source unit and the photocatalyst filter are kept constant.

The experiment data shown in FIG. 8 were obtained using one light source and one photocatalyst filter according to an embodiment of the present disclosure. Specifically, the photocatalyst filter had a size of about 33 mm length, about 33 mm width, and about 10 mm thickness, and the light source was configured to emit light having a wavelength of about 365 nm upon application of an electric current of 300 mA. A fan was disposed at the rear side of a light emitting diode to force a fluid to flow towards the photocatalyst filter. The fan was driven at 12V and forces the fluid to flow at a flow rate of 0.12 m$^3$/min.

FIG. 8 shows data of purification rates of 10 ppm ammonia gas for 180 min under conditions that the light emitting diode was not operated and that the separation distance between the light emitting diode and the photocatalyst filter was set to 10 mm, 20 mm, 30 mm, and 40 mm.

As a result of experiment, when the separation distance was about 10 mm, about 32.1% of ammonia could be removed in about 3 hours, and when the separation distance was about 20 mm, about 35.3% of ammonia could be removed in 3 hours. In addition, when the separation distance was about 30 mm, about 30.5% of ammonia could be removed, and when the separation distance was about 40 mm, about 28.0% of ammonia could be removed.

From the above result, it was determined that, when the separation distance between the light source and the photocatalyst filter was set to about 20 mm, the maximum area of the photocatalyst filter could be irradiated with a sufficient intensity of light to activate the photocatalyst filter. The intensity of light and irradiation area according to the separation distance between the light source and the photocatalyst filter were set as listed in Table 1.

TABLE 1

| Separation distance | Diameter of irradiated region | Area of irradiated region | Irradiation intensity per unit area |
|---|---|---|---|
| 10 mm | 34.64 mm | 9.42 cm$^2$ | 21.72 mW/cm$^2$ |
| 20 mm | 69.28 mm | 37.68 cm$^2$ | 20.23 mW/cm$^2$ |
| 30 mm | 103.92 mm | 84.78 cm$^2$ | 15.52 mW/cm$^2$ |
| 40 mm | 138.56 mm | 150.71 cm$^2$ | 11.81 mW/cm$^2$ |

As can be seen from Table 1, when the separation distance between the light source and the photocatalyst filter was set to about 20 mm, it was possible to secure sufficient intensity (about 20.23 mW/cm$^2$) of light to activate the light photocatalyst filter. When the separation distance was set to about 10 mm, the intensity of light was higher than the intensity of light at the separation distance set to 20 mm and the irradiated area was significantly reduced to about ¼.

Accordingly, it was determined that, when the separation distance between the light source and the photocatalyst filter was set to about 20 mm, the maximum area of the photocatalyst filter could be irradiated with a sufficient intensity of light to activate the photocatalyst filter, and such determination could be proved based on difference in ammonia removal efficiency shown in FIG. 8.

Figure 9:
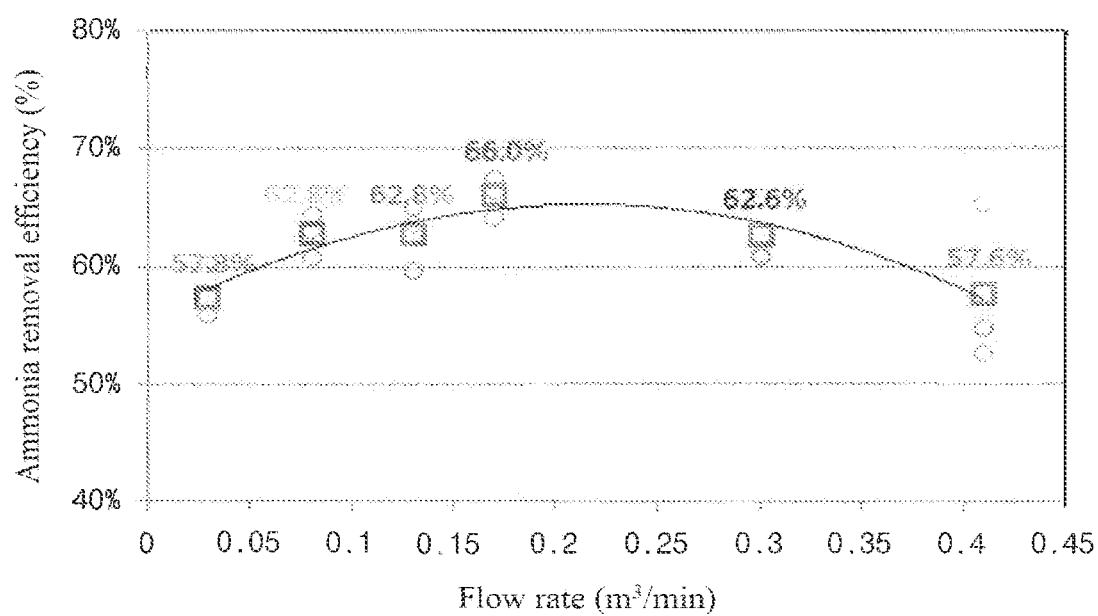
FIG. 9 is a graph depicting ammonia removal efficiency depending on flow speed.

FIG. 9 is a graph depicting ammonia removal efficiency depending on flow rate.

The experiment data shown in FIG. 9 were obtained using the fluid processing module shown in FIG. 6, which was provided with one photocatalyst filter and three light sources. Specifically, the photocatalyst filter had a size of about 55 mm length, about 55 mm width, and about 10 mm thickness, and the light sources were configured to emit light having a wavelength of about 365 nm upon application of an electric current of 250 mA. The distance between the photocatalyst filter and the light sources was set to 20 mm and the intensity of light per unit area of the photocatalyst filter was set to about 20.0 mW/cm$^2$.

From FIG. 9, it could be seen that the ammonia removal rate was changed depending upon the flow rate. It could be seen that the flow rate in an effective range for achieving an effective deodorization efficiency of about 60% was in the range of about 0.06 m$^3$/min to about 0.37 m$^3$/min. Accordingly, the shape of the guide portion and the operating intensity of the fan may be changed such that the flow rate in the region of the flow channel where the photocatalyst filter was disposed was in an effective range of about 0.06 m$^3$/min to about 0.37 m$^3$/min.

For example, when the flow rate of the fluid entering the fluid processing module is less than about 0.06 m$^3$/min, the guide portion may be provided to the region where the photocatalyst filter is disposed, in order to increase the flow rate in the region where the photocatalyst filter is disposed. On the contrary, when the flow rate of the fluid entering the fluid processing module is greater than about 0.37 m$^3$/min, the guide portion may be provided to the main body inlet and/or the main body outlet in order to decrease the flow rate in the region where the photocatalyst filter is disposed.

Figure 10:
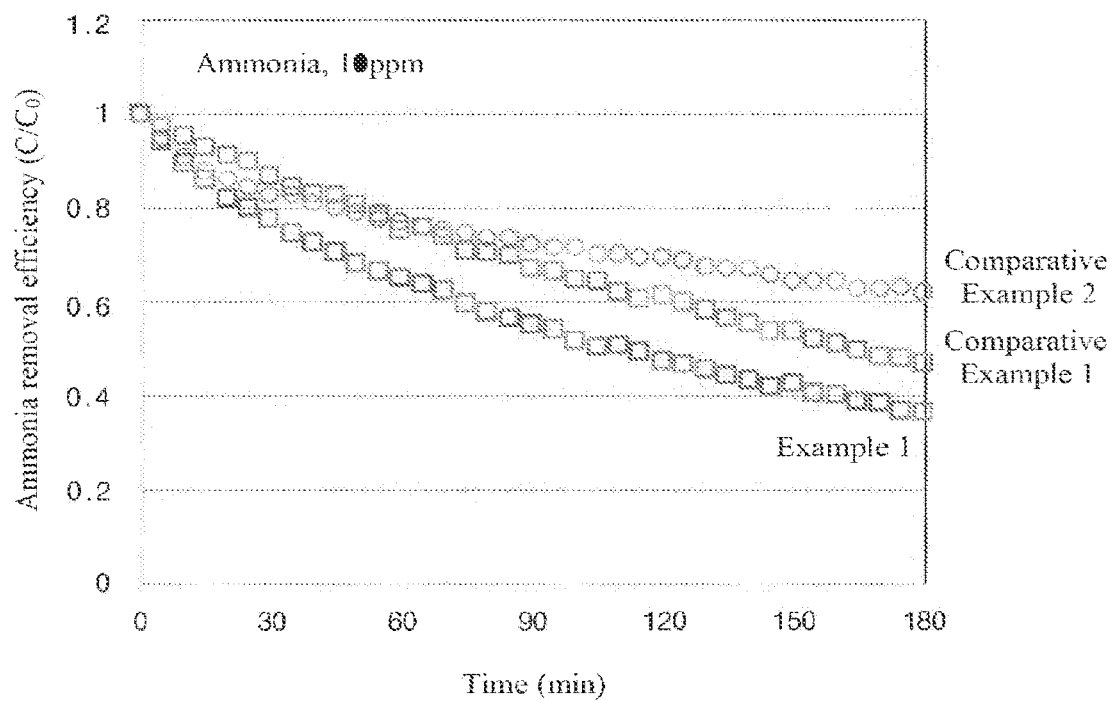
FIG. 10 is a graph depicting ammonia removal efficiency of fluid processing modules according to examples and comparative examples.

FIG. 10 is a graph depicting ammonia removal efficiency of fluid processing modules according to examples and comparative examples.

In Example 1, the absorption filter was disposed perpendicular to the flow direction of the fluid and the guide portion was disposed in the main body, as shown in FIG. 1. In Comparative Example 1, the absorption filter was disposed perpendicular to the flow direction of the fluid and the guide portion was not disposed in the main body. In Comparative Example 2, the absorption filter was provided parallel to the flow of the fluid without the guide portion.

In Example 1 and Comparative Examples 1 and 2, about 250 mA was applied to each of three light sources emitting light having a wavelength of about 365 nm in order to secure an irradiation intensity of about 20.0 mW/cm$^2$ per unit area of the photocatalyst filter. Further, in Example 1 and Comparative Examples 1 and 2, the photocatalyst filter was disposed parallel to the flow direction of the fluid and had a size of 55 mm length, 55 mm width, and 10 mm thickness. The absorption filter had a size of 35 mm×35 mm×10 mm (length×width×thickness).

Table 2 shows ammonia removal efficiency of the fluid processing modules of Example 1 and Comparative Examples 1 and 2.

TABLE 2

| Time | Example 1 | Comparative Example 1 | Comparative Example 2 |
|---|---|---|---|
| 0 | — | — | — |
| 30 min | 22.5% | 13.4% | 17.2% |
| 60 min | 34.8% | 24.6% | 23.1% |
| 120 min | 52.6% | 38.5% | 30.7% |
| 180 min | 63.2% | 52.9% | 38.0% |

As can be seen from Table 2 and FIG. 10, it could be seen that the fluid processing module of Example 1 achieved effective deodorization efficiency between 120 minutes and 180 minutes after the fluid processing module was started to operate. However, it could be seen that the fluid processing modules of Comparative Examples 1 and 2 could not achieve effective deodorization efficiency. Accordingly, it can be confirmed that effective deodorization efficiency can be secured by providing the guide portion and placing the absorption filter perpendicular to the flow direction of the fluid.

In the above description, the structure and effects of the fluid processing module are described. The fluid processing module according to the embodiment of the present disclosure may be applied to a storage device. Next, a storage device including a fluid processing module according to an embodiment of the present disclosure will be described in detail.

Figure 11:
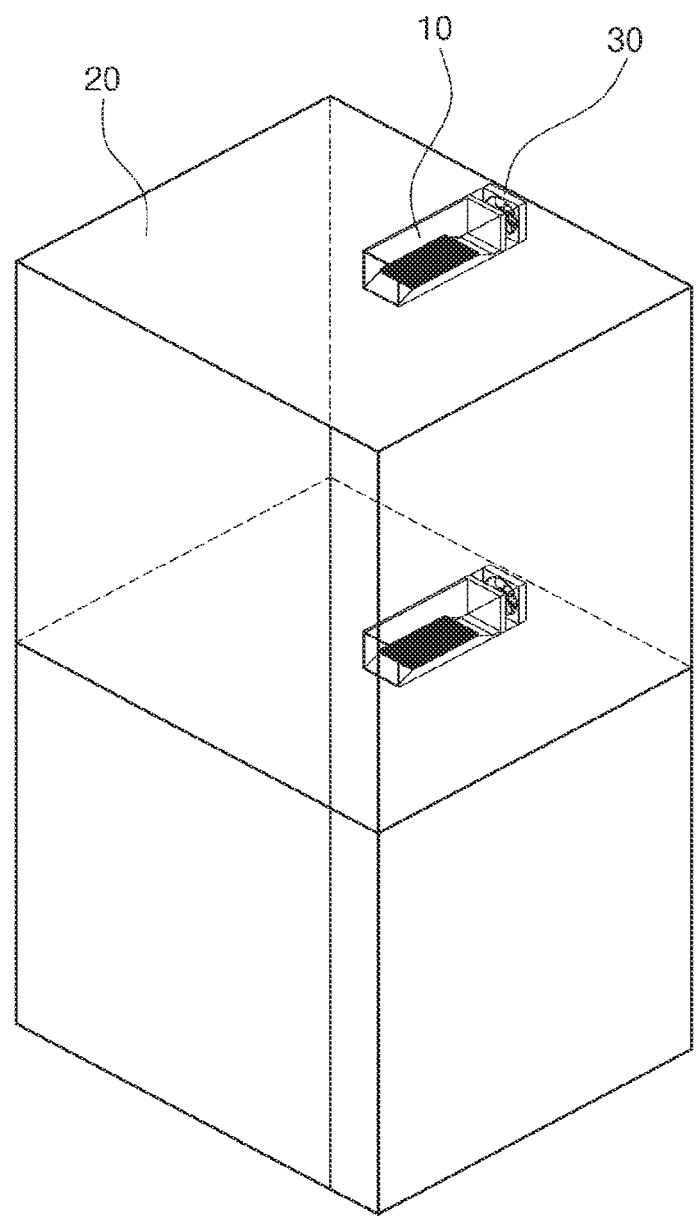
FIG. 11 is a perspective view of a storage device including a fluid processing module according to an embodiment of the present disclosure.

FIG. 11 is a perspective view of a storage device including a fluid processing module according to an embodiment of the present disclosure.

Referring to FIG. 11, the storage device includes a casing 20 having a storage space therein and the fluid processing module 10 provided to the casing 20.

The casing 20 is a storage box and may be of various kinds, such as closets, refrigerators, and the like. The casing 20 may be formed of various plastic materials, such as polypropylene (PP), polyethylene (PE), polycarbonate (PC), polystyrene (PS), polyvinyl chloride (PVC), polyamide (PA), polyethylene terephthalate (PET), polybutylene terephthalate (PBT), polyethylene adipic acid (PEA), polybutylene succinate (PBS), polyacetal, polyphenylene oxide, ABS resin, melamine resin, urethane resin, fluorine resin, and the like; or various metals, such as stainless steel, aluminum, and carbon steel.

The fluid processing module 10 is disposed at one side of the casing 20 to purify a fluid (for example, air) inside the casing 20. Specifically, inside the casing 20, air flows into the fluid processing module 10 and is discharged therefrom after the air is subjected to deodorization and sterilization inside the fluid processing module 10. As the fluid is circulated to pass through the fluid processing module 10, the fluid inside the casing 20 can be uniformly subjected to deodorization and sterilization.

The fluid processing module 10 may be disposed in plural. The multiple fluid processing modules 10 may be disposed in different regions of the casing 20. For example, for the casing 20 including multiple compartments partitioned from each other, the fluid processing module 10 may be provided to each of the compartments.

In some embodiments, the casing 20 may be further provided with a casing fan 30. The casing fan 30 may promote circulation of a fluid by forcing the fluid to flow towards the fluid processing modules 10 inside the casing 20. As a result, deodorization and sterilization of the fluid can be more rapidly and uniformly achieved inside the casing 20.

The storage device according to the embodiment includes the fluid processing module 10, thereby maintaining the interior of the storage device clean even in the case where the interior of the storage device is closed. Furthermore, since the fluid processing module 10 has a compact structure, the storage device can secure a sufficient storage space even with the multiple fluid processing modules 10 therein.

Although some embodiments have been described herein, it should be understood that various modifications, changes, alterations, and equivalents can be made by those skilled in the art without departing from the spirit and scope of the invention.

Therefore, the scope of the present disclosure is not limited to the detailed description herein and should be defined only by the accompanying claims and equivalents thereto.

What is claimed is:

1. A fluid processing module comprising:
a main body having:
an inlet through which a fluid enters;
a flow channel extending in a first direction therein and allowing the fluid to flow therein; and
an outlet through which the fluid is discharged and connected to the inlet via the flow channel;
an absorption filter disposed substantially perpendicular to the first direction inside the main body;
a photocatalyst filter disposed parallel to the first direction inside the main body; and
a light source unit disposed inside the main body and emitting light towards the photocatalyst filter configured to perform a photocatalytic reaction that generates superoxide anions and hydroxyl radicals,
wherein the flow channel has a first region including an inlet of the flow channel and having a first cross-sectional area, a third region including an outlet of the flow channel, a second region disposed between the first region and the third region and having a second cross-sectional area, wherein the absorption filter is disposed in the first region and the photocatalyst filter is disposed in the second region, the photocatalyst filter exhibiting a predetermined level of deodorization efficiency when the fluid passes through the photocatalyst filter at a predetermined range of flow speeds;
wherein the fluid flows at a first flow speed in the first cross-sectional area and at a second flow speed in the second cross-sectional area; and
wherein the flow channel has a shape that allows the second flow speed to be greater than the first flow speed in response to the fluid entering the flow channel is less than the predetermined range and the first cross-sectional area is greater than the second cross-sectional area; and
wherein the third region has a cross-sectional area that is greater than the second cross-sectional area and increases in the first direction.

2. The fluid processing module according to claim 1, wherein the main body further comprises a guide portion defining size and shape of the flow channel.

3. The fluid processing module according to claim 2, wherein the light source unit is disposed on the guide portion to face the photocatalyst filter.

4. The fluid processing module according to claim 1, wherein a distance between the light source unit and the photocatalyst filter ranges from 15 mm to 25 mm.

5. The fluid processing module according to claim 1, wherein the predetermined level of deodorization efficiency corresponds to a pollutant removal efficiency of 60% or more by the photocatalyst filter.

6. The fluid processing module according to claim 1, wherein
the flow channel further comprises:
a first region including an inlet of the flow channel and having a first width varying in the first direction;
a second region disposed adjacent to the first region and having a second width that is constant; and
a third region including an outlet of the flow channel and having a third width varying in the first direction.

7. The fluid processing module according to claim 6, wherein the first width gradually decreases in the first direction and the second width of the second region is same as the width of the second cross-sectional area.

8. The fluid processing module according to claim 6, wherein the photocatalyst filter is disposed in the second region.

9. The fluid processing module according to claim 6, wherein the absorption filter is disposed in the first region or the third region.

10. The fluid processing module according to claim 1, further comprising: a fan disposed in the flow channel of the main body.

11. The fluid processing module according to claim 1, wherein the photocatalyst filter has a shape extending in the first direction.

12. The fluid processing module according to claim 1, wherein light emitted from the light source unit includes light in a wavelength band of 315 nm to 400 nm.

13. The fluid processing module according to claim 1, wherein the light source unit further comprises multiple light sources and at least two of the multiple light sources emit light in different wavelength bands.

14. The fluid processing module according to claim 13, wherein at least two of the multiple light sources emit light having wavelengths in a wavelength band of 100 nm to 280 nm.

15. The fluid processing module according to claim 1, wherein a product of a value of the first cross-sectional area and the first flow speed is the same as a product of a value of the second cross-sectional area and the second flow speed.

16. A storage device comprising:
a casing having a storage space therein; and
a fluid processing module disposed in a casing, the fluid processing module comprising:
a main body having a flow channel extending in a first direction;
an absorption filter disposed substantially perpendicular to the first direction inside the main body;

a photocatalyst filter disposed parallel to the first direction inside the main body; and a light source unit disposed inside the main body and emitting light towards the photocatalyst filter configured to perform a photocatalytic reaction that generates superoxide anions and hydroxyl radicals, wherein the flow channel has a first region including an inlet of the flow channel and having a first cross-sectional area, a third region including an outlet of the flow channel, a second region disposed between the first region and the third region and having a second cross-sectional area in a region where, wherein the absorption filter is disposed in the first region and the photocatalyst filter is disposed in the second region, the photocatalyst filter exhibiting a predetermined level of deodorization efficiency when the fluid passes through the photocatalyst filter at a predetermined range of flow speeds;

wherein a fluid flows at a first flow speed in the region of the flow channel having the first cross-sectional area and at a second speed in the region of the flow channel having the second cross-sectional area; and wherein the flow channel has a shape that allows the second flow speed to be greater than the first flow speed in response to the fluid entering the flow channel is less than the predetermined range and the first cross-sectional area is greater than the second cross-sectional area; and wherein the third region has a cross-sectional area that is greater than the second cross-sectional area and increases in the first direction.

17. The storage device according to claim 16, further comprising:

a fan circulating air inside the storage space, wherein the fan forces the air to flow towards the fluid processing module inside the casing.

18. The storage device according to claim 16, further comprising two or more fluid processing modules.

* * * * *